United States Patent
Doebler, II et al.

(10) Patent No.: US 8,784,736 B2
(45) Date of Patent: *Jul. 22, 2014

(54) SYSTEMS AND DEVICES FOR ISOTHERMAL BIOCHEMICAL REACTIONS AND/OR ANALYSIS

(75) Inventors: Robert W. Doebler, II, Upland, CA (US); Christopher Cooney, Severn, MD (US); Anna Hickerson, Altadena, CA (US); James D. Sterling, Upland, CA (US); Ali Nadim, San Marino, CA (US)

(73) Assignee: Keck Graduate Institute, Claremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/415,709

(22) Filed: Mar. 8, 2012

(65) Prior Publication Data

US 2012/0171756 A1 Jul. 5, 2012

Related U.S. Application Data

(63) Continuation of application No. 12/052,950, filed on Mar. 21, 2008, now Pat. No. 8,153,064.

(60) Provisional application No. 60/896,452, filed on Mar. 22, 2007.

(51) Int. Cl.
*G01N 21/64* (2006.01)

(52) U.S. Cl.
USPC ........ 422/82.08; 422/400; 422/401; 422/402; 422/403; 422/404; 422/82.05; 422/82.06; 422/82.07; 422/82.09; 436/164; 436/172; 436/174; 436/55; 73/864.91; 73/863.11; 435/286.1

(58) Field of Classification Search
USPC .......... 422/400–404, 82.05–82.09, 560–563, 422/565–566, 68.1; 436/164, 172, 174, 55; 73/864.91, 863.11
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 5,229,580 A | 7/1993 | Chioniere | |
| 5,315,993 A | 5/1994 | Alcala | |
| 5,464,773 A | 11/1995 | Melendez et al. | |

(Continued)

FOREIGN PATENT DOCUMENTS

| | | |
|---|---|---|
| EP | 1 767 630 A1 | 3/2007 |
| JP | 7-114718 B2 | 12/1995 |

(Continued)

OTHER PUBLICATIONS

Belgrader et al., "A Minisonicator to Rapidly Disrupt Bacterial Spores for DNA Analysis," Anal. Chem. 71:4232-4236, 1999.

(Continued)

*Primary Examiner* — Jyoti Nagpaul
(74) *Attorney, Agent, or Firm* — Seed IP Law Group PLLC (57) ABSTRACT

An isothermal reaction and analysis system may include a receiver to receive sample holders, a thermal control subsystem to control a temperature of the receiver, an excitation subsystem, a detection subsystem and an analysis subsystem. Excitation sources and/or detectors are positioned to enhance data collection. Sample holders may include filters, selectively blocking and passing wavelengths or bands of electromagnetic radiation.

21 Claims, 3 Drawing Sheets

(56) References Cited

U.S. PATENT DOCUMENTS

| | | | |
|---|---|---|---|
| 5,475,610 | A | 12/1995 | Atwood et al. |
| 5,824,517 | A | 10/1998 | Cleuziat et al. |
| 6,084,683 | A | 7/2000 | Bruno et al. |
| 6,369,893 | B1 | 4/2002 | Christel et al. |
| 6,455,287 | B1 | 9/2002 | Jem |
| 6,680,025 | B2 | 1/2004 | Hearst et al. |
| 6,740,518 | B1 | 5/2004 | Duong et al. |
| 6,976,383 | B2 | 12/2005 | Petro et al. |
| 7,315,376 | B2 | 1/2008 | Bickmore et al. |
| 8,153,064 | B2 | 4/2012 | Doebler, II et al. |
| 2001/0012612 | A1 | 8/2001 | Petersen et al. |
| 2002/0109844 | A1 | 8/2002 | Christel et al. |
| 2002/0146836 | A1 | 10/2002 | Neilson et al. |
| 2002/0155619 | A1 | 10/2002 | Kurihara et al. |
| 2003/0082590 | A1 | 5/2003 | Van Ness et al. |
| 2003/0104431 | A1 | 6/2003 | Van Ness et al. |
| 2003/0138800 | A1 | 7/2003 | Van Ness et al. |
| 2003/0165911 | A1 | 9/2003 | Van Ness et al. |
| 2004/0252299 | A9 | 12/2004 | Lemmo et al. |
| 2005/0156124 | A1 | 7/2005 | Tobimatsu |
| 2005/0269522 | A1 | 12/2005 | Farmer et al. |
| 2006/0019265 | A1 | 1/2006 | Song et al. |
| 2006/0030038 | A1 | 2/2006 | Taylor et al. |
| 2006/0240462 | A1 | 10/2006 | Todd et al. |
| 2007/0035818 | A1 | 2/2007 | Bahatt et al. |
| 2007/0248958 | A1 | 10/2007 | Jovanovich et al. |
| 2010/0178697 | A1 | 7/2010 | Doebler et al. |

FOREIGN PATENT DOCUMENTS

| | | |
|---|---|---|
| JP | 2650159 B2 | 5/1997 |
| JP | 2710159 B2 | 10/1997 |
| KR | 10-0700093 | 3/2007 |
| WO | 95/25180 A1 | 9/1995 |
| WO | 99/09211 A1 | 2/1999 |
| WO | 99/49081 A2 | 9/1999 |
| WO | 00/28082 A1 | 5/2000 |
| WO | 2009/089466 A2 | 7/2009 |

OTHER PUBLICATIONS

DeAngelis et al., "Solid-phase reversible immobilization for the isolation of PCR products," Nucleic Acids Research 23(22):4742-4743, 1995.

Doebler et al., "System, Apparatus and Method for Lysing" U.S. Appl. No. 61/020,072, filed Jan. 9, 2008, 62 pages.

Doebler et al., "Continuous-Flow, Rapid Lysis Devices for Biodefense Nucleic Acid Diagnostic Systems," JALA 14:119-125, 2009.

Doebler et al., "Effect of Triton X-100 on Nicking Endonuclease Activity of N.BstNBI during Isothermal Exponential Amplification of Oligonucleotides Performed Using a Hand-held Real-time Fluorescence-based Device," Keck Graduate Institute, Poster presented in 2005, 1 page.

Doebler et al., "System, Apparatus and Method for Material Preparation and/or Handling" U.S. Appl. No. 12/732,070, Preliminary Amendment, filed Mar. 29, 2010, 3 pages.

Doebler et al., "Systems and Devices for Isothermal Biochemical Reactions and/or Analysis," Office Action dated Apr. 28, 2010, for U.S. Appl. No. 12/052,950, 20 pages.

Doebler et al., "Systems and Devices for Isothermal Biochemical Reactions and/or Analysis," Amendment dated Aug. 18, 2010, for U.S. Appl. No. 12/052,950, 18 pages.

Doebler et al., "Systems and Devices for Isothermal Biochemical Reactions and/or Analysis," Office Action dated Nov. 24, 2010, for U.S. Appl. No. 12/052,950, 22 pages.

Doebler et al., "Systems and Devices for Isothermal Biochemical Reactions and/or Analysis," Amendment dated Feb. 24, 2011, for U.S. Appl. No. 12/052,950, 13 pages.

Doebler et al., "Systems and Devices for Isothermal Biochemical Reactions and/or Analysis," Office Action dated May 10, 2011, for U.S. Appl. No. 12/052,950, 22 pages.

Doebler et al., "Systems and Devices for Isothermal Biochemical Reactions and/or Analysis," Amendment dated Nov. 10, 2011, for U.S. Appl. No. 12/052,950, 9 pages.

Farmer et al., "Hand-held thermal-regulating fluorometer," Review of Scientific Instruments 76(115102):1-5, 2005.

International Search Report for International Application No. PCT/US2009/030622, mailed Aug. 27, 2009, 4 pages.

International Search Report for International Application No. PCT/US2010/039872, mailed Mar. 23, 2011, 6 pages.

Irvine et al., "Capture and Elution of Bio-Analytes Via Beads That Are Used to Disrupt Specimens" U.S. Appl. No. 61/220,984, filed Jun. 26, 2009, 67 pages.

Irvine et al., "Capture and Elution of Bio-Analytes Via Beads That Are Used to Disrupt Specimens" U.S. Appl. No. 61/317,604, filed Mar. 25, 2010, 91 pages.

Kim et al., "Cell lysis on a microfluidic CD (compact disc)," Lab Chip 4:516-522, 2004.

Paul et al., "A Multichannel Handheld Sensor for Microbial Contaminants," CICEET Progress Report for the period Mar. 16, 2006 through Sep. 15, 2006, URL=http://ciceet/unh.edu/progressreports/2006/9_2006/paul05/, download date Nov. 1, 2011, 3 pages.

US Digital Designs, DNA Amplifier, URL=http://usdd.com/Display_Page.php?pageTitle=DNA%20Amplifier, download date Nov. 1, 2011, 1 page.

Written Opinion for International Application No. PCT/US2009/030622, mailed Aug. 27, 2009, 4 pages.

Written Opinion for International Application No. PCT/US2010/039872, mailed Mar. 23, 2011, 4 pages.

SYSTEMS AND DEVICES FOR ISOTHERMAL BIOCHEMICAL REACTIONS AND/OR ANALYSIS

CROSS REFERENCE TO RELATED APPLICATIONS

This application is a continuation of U.S. patent application Ser. No. 12/052,950, filed Mar. 21, 2008, which claims benefit under 35 U.S.C. 119(e) to U.S. provisional patent application Ser. No. 60/896,452, filed Mar. 22, 2007, which is incorporated herein by reference in its entirety.

BACKGROUND

1. Field

This disclosure generally relates to systems and devices for isothermal biochemical reactions, for example nucleic acid amplification or cell growth, and/or analytic equipment to analyze the products or results of such biochemical reactions.

2. Description of the Related Art

There are a number of known techniques to perform biochemical reactions, for example to amplify nucleic acids such as DNA and RNA.

One of the primary existing techniques is polymerase chain reaction (PCR) method, such as that described in U.S. Pat. Nos. 4,683,195; 4,683,202; and 4,800,159. Another existing technique is reverse transcription (RT) PCR. Other techniques include ligase chain reaction (LCR) and transcription-based amplification system (TAS).

These techniques each require repeating a set of reactions for each sample at two or more distinctly different temperatures, commonly known as thermal cycling. These techniques typically require strict control over a wide range of temperatures. There are a number of thermal cycling devices on the market. It is commercially desirable that these thermal cycling devices be capable of rapidly adjusting between the desired reaction temperatures in order to increase the number of reactions per unit of time, thereby increasing throughput and reducing costs associated with operation of such thermal cycling devices. The need to strictly control temperature over a wide range with a fast response time causes these thermal cycling devices to be expensive, for example costing between $40,000 and $60,000. Due to these requirements, thermally cycling device are also large, and are not suitable to being provided in portable or handheld forms.

Amplification techniques that avoid thermal cycling are becoming more popular. For example, strand displacement amplification (SDA) such as described in Japanese Examined Patent Application No. JP-B7-114718 and various modifications of SDA such as described in U.S. Pat. No. 5,824,517 and International Patent Application Nos. WO99/09211; WO95/25180 and WO99/49081. Also for example, self-sustained replication (3SR), nucleic acid sequence based amplification (NASBA) such as described in Japanese Patent No. 2650159, transcription mediated amplification (TMA), and Q beta replicase method such as described in Japanese Patent No. 2710159. Further examples include loop mediated isothermal amplification (LAMP) such as described in WO00/28082 and exponential amplification reaction (EXPAR) such as described in U.S. Patent Application Publication Nos. 2003/0082590, 20003/0104431; 2003/0138800 and 2003/0165911.

It is common to employ thermal cycling devices to perform isothermal biochemical reactions, even though thermal cycling is not required for such isothermal processes. However, as noted above, devices capable of thermal cycling are prohibitively expensive. Such devices are also typically large, and not portable or suitable to handheld formats.

A number of analytic devices exist to analyze samples that have been subjected to biochemical reactions such as nucleic acid amplification. Such analytic devices typically employ laser or monochromator based excitation systems. Such devices are typically large and expensive.

Commercial acceptance of alternative amplification techniques is dependent on a variety of factors, such as the cost of suitable devices, speed of operation and effectiveness in performing amplification and/or analysis. Commercial acceptance may also depend on the portability of isothermal reaction and/or analysis devices. Commercial acceptance may additionally, or alternatively be dependent on the ability for an isothermal reaction and/or analysis device to work with existing sample holders, avoiding the need to stock multiple types of sample holders or the need to replace existing stocks of sample holders. Therefore, it may be desirable to have novel biochemical reaction and/or analysis devices. The present disclosure is directed to overcoming one or more of the shortcomings set forth above, and providing further related advantages.

BRIEF SUMMARY

In one aspect, the present disclosure is directed to a system to support biochemical reactions that includes a receiver having a plurality of receptacles formed therein, each of the receptacles sized to at least partially receive and support a respective one of a plurality of sample holders; an excitation subsystem including at least a first plurality of excitation sources positioned at least partially in the receiver to direct electromagnetic energy toward at least a portion of a respective one of the sample holders received in a respective one of the receptacles of the receiver, the excitation subsystem operable to excite with the electromagnetic energy each of a number of samples contained in respective ones of a plurality of the sample holders while the sample holders are received and supported by the receiver; a detection subsystem that includes a plurality of detectors, each of the detectors positioned to detect emission of electromagnetic energy from a respective sample contained in a respective one of the sample holders that are received and supported by the receiver; and a thermal control subsystem operable to at least approximately maintain a temperature of the receiver at least approximately constant for a period of time sufficient to perform an isothermal reaction on the samples. This may include heater and a heat removal mechanism or a cooler or cooling mechanism that may involve passive and/or active cooling approaches. The excitation subsystem may include a second plurality of excitation sources, each of the excitation sources of the second plurality of excitation sources positioned at least partially in the receiver to direct the electromagnetic energy toward at least a portion of a respective one of the sample holders received in a respective one of the receptacles of the receiver, the electromagnetic energy directed by the excitation sources of the second plurality of excitation sources being of a different wavelength than the electromagnetic energy directed by the excitation sources of the first plurality of excitation sources. The excitation sources may advantageously be positioned in a respective passage in the receiver to direct the electromagnetic energy toward only a base portion of the respective sample holder when the sample holder is positioned in the respective one of the receptacles, the base portion at least proximate a bottom of the sample holder when supported by the receiver. A filter may be positioned between the excitation sources and the respective sample holders. A filter may be positioned between the detectors and the respective sample holders, for example to filter at least a portion of the electromagnetic energy emitted by at least one of the excitation sources. The thermal control subsystem may includes a temperature sensor to detect a temperature of a biochemical reaction or the receiver and may include a heater element operable to provide heat to the receiver and/or a cooling element to withdraw heat from the receiver in response to a difference between the detected temperature and a set temperature. In contrast to thermal cycling devices, the receiver may have a large thermal mass with respect to the samples. The receptacles may be spaced from one another by a distance selected from 2.25 mm, 4.5 mm and 9 mm.

In another aspect, the system may include at least one controller configured to modulate or pulsate the excitation sources and to select a component of a response signal from the detection elements based on the modulation or pulsation of the excitation sources. The at least one controller may be configured to perform Fourier transformation on the response signal to improve a signal-to-noise ratio of the system.

In another aspect, the system may include at least one controller configured to modulate or pulsate the excitation sources at respective frequencies and to select a component of a response signal from the detection elements based on the modulation or pulsation of the excitation sources. For example, there may two excitation sources and one detector per receptacle, each of the excitation sources emitting at different wavelengths. In such an embodiment, the at least one controller may be configured to operate the excitation sources at different frequencies, and to demodulate a response signal based on the frequencies. The at least one controller may be configured to determine information about different biochemical reactions occurring in the same receptacle based on the demodulated response signal. The at least one controller may be configured to vary a current supplied to the excitation sources to cause each of the excitation sources to emit at different wavelengths at different times.

In another aspect, the present disclosure is directed to a sample holder for use with a system that excites a sample received in the sample holder with optical electromagnetic energy and detects optical electromagnetic energy returned by the sample, the sample holder including a wall member at least a portion of which provides an optical path between an exterior of the sample holder and an interior of the sample holder that filters a first band of wavelengths of optical electromagnetic energy in a range of optical electromagnetic energy emitted by an excitation source of a system and passes a second band of wavelengths of optical electromagnetic energy detectable by a detector of the system, where optical electromagnetic energy consists of electromagnetic energy between an ultraviolet and an infrared portion of the electromagnetic spectrum, inclusive.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements, as drawn, are not intended to convey any information regarding the actual shape of the particular elements, and have been solely selected for ease of recognition in the drawings.

DETAILED DESCRIPTION

In the following description, certain specific details are included to provide a thorough understanding of various disclosed embodiments. One skilled in the relevant art, however, will recognize that embodiments may be practiced without one or more of these specific details, or with other methods, components, materials, etc. In other instances, well-known structures associated with temperature control including but not limited to voltage and/or current regulators, excitation, detection, and/or signal and/or data processing, have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment," or "an embodiment," or "in another embodiment" means that a particular referent feature, structure, or characteristic described in connection with the embodiment is included in at least one embodiment. Thus, the appearance of the phrases "in one embodiment," or "in an embodiment," or "in another embodiment" in various places throughout this specification are not necessarily all referring to the same embodiment. Furthermore, the particular features, structures, or characteristics may be combined in any suitable manner in one or more embodiments.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings provided herein are for convenience only and do not interpret the scope or meaning of the embodiments.

Figure 1:
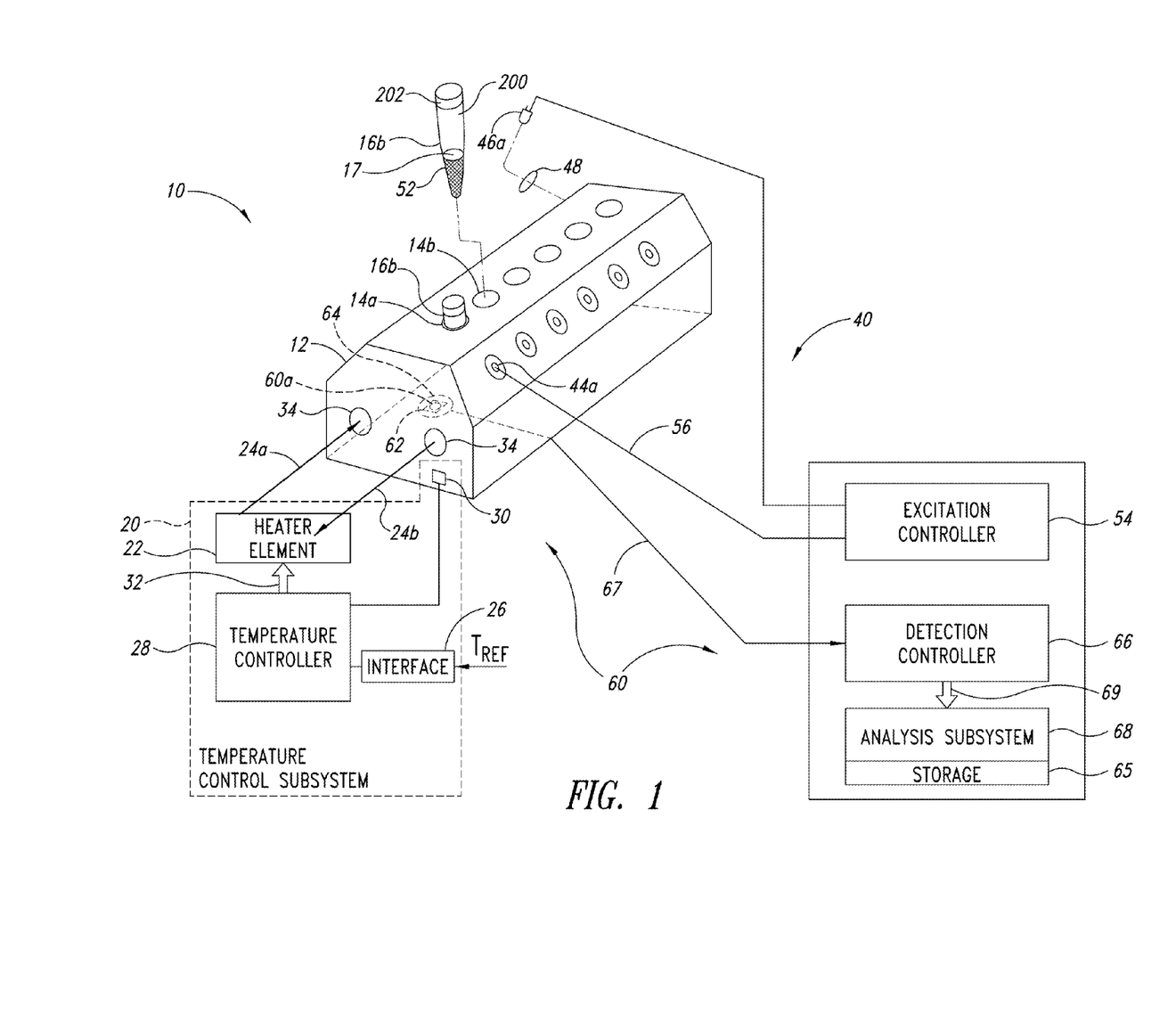
FIG. 1 is a diagrammatic view of an isothermal reaction and analysis system including a receiver to receive sample holders, a thermal control subsystem, an excitation subsystem, a detection subsystem and an analysis subsystem, according to one illustrated embodiment.
Figure 2A:
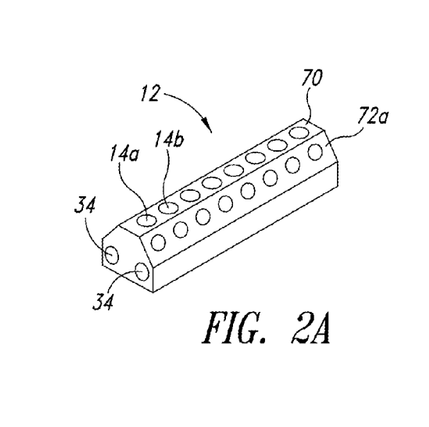
FIG. 2A is a top, front, left side isometric view of a receiver of an isothermal reaction and analysis system, according to one illustrated embodiment.
Figure 2B:
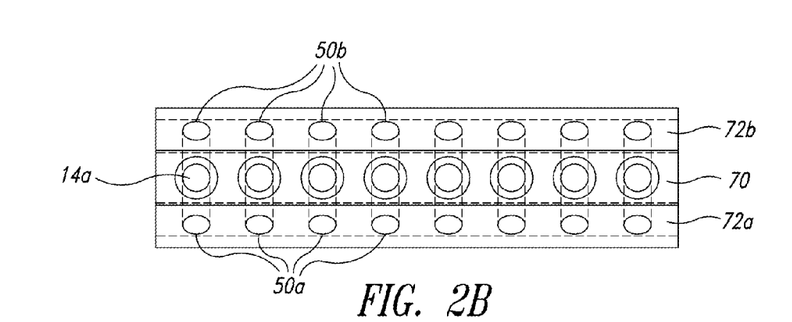
FIG. 2B is a top plan view of the receiver of FIG. 2A.
Figure 2C:
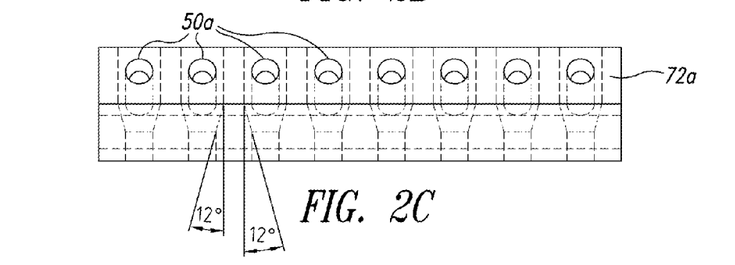
FIG. 2C is a front elevational view of the receiver of FIG. 2A.
Figure 2D:
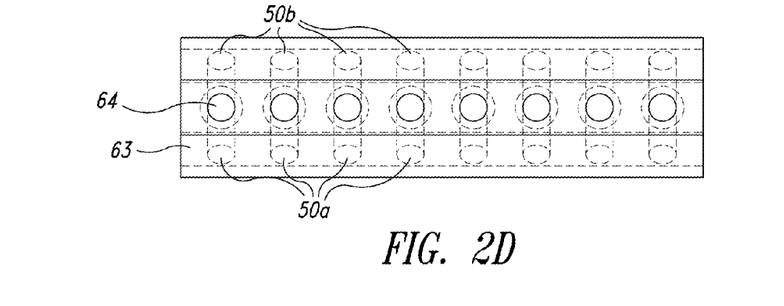
FIG. 2D is a bottom plan view of the receiver of FIG. 2A.
Figure 2E:
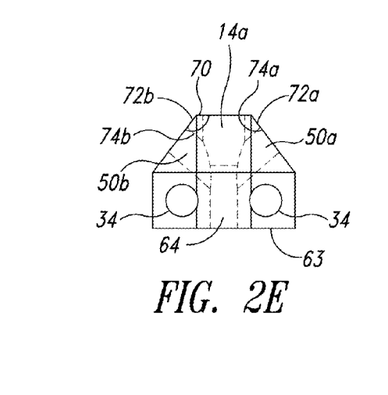
FIG. 2E is a side elevational view of the receiver of FIG. 2A.

FIG. 1 shows a system 10 to support isothermal biochemical reactions, for example isothermal amplification nucleic acids and/or isothermal cell growth using inserted fluorescent proteins (FPs), for example Blue FPs or Green FPs, according to one illustrated embodiment.

The isothermal reaction and analysis system 10 includes a receiver 12 having a plurality of receptacles 14a, 14b (only two called out in the Figure, collectively referenced as 14)

formed therein. Each of the receptacles 14 is sized to at least partially receive and support a respective one of a plurality of sample holders 16a, 16b, (only two illustrated, collectively referenced as 16). In FIG. 1, one sample holder 16a is illustrated received in a respective receptacle 14a and the second sample holder 16b is illustrated removed from the respective receptacle 14.

The isothermal reaction system 10 also includes a thermal control subsystem 20 operable to at least approximately maintain a temperature at least proximate the sample holders 14. In particular, the thermal control subsystem 20 maintains a temperature of the receiver 12 approximately constant at a desired or set temperature, for a period of time sufficient to perform an isothermal reaction on the samples 17 held by the sample holders 16.

The thermal control subsystem 20 may include one or more heater elements 22 operable to provide heat (indicated by arrow 24a) to the receiver 12 and/or one or more cooling elements operable to withdraw heat from the receiver 12, in response to a difference between the detected temperature and at least one set temperature. In some embodiments the heater element 22 may recycle heat (indicated by arrow 24b) from the receiver 12. In some embodiments, the at least one heater element 22 is conductively thermally coupled to the receiver 12 to provide heat to the sample holders 14 via the receiver 12. In some embodiments, the one or more cooling element is conductively thermally coupled to the receiver 12 to withdraw heat from the sample holders 14 via the receiver 12. As discussed below, in some embodiments the receiver 12 has a large thermal mass (i.e., specific heat capacity multiplied by mass) with respect to the samples 17 to facilitate stable, constant and uniform temperature operation, which is useful in performing isothermal reactions. The heater element 22 may take any of a variety of forms including resistors or resistive elements, radiant elements or other sources of heat. For example, the heater element 22 may take the form of a thin-film KAPTON heater with an aluminum foil backing, commercially available from Minco. Such a heater element 22 may be directly positioned on or attached to the receiver 12. The cooling elements may likewise take a variety of forms including refrigerator coils and/or heat sinks.

The thermal control subsystem 20 may further include an interface 26 to receive an indication (indicated by arrow $T_{REF}$) of a desired or set temperature for the reactions. In some embodiments, the thermal control subsystem 20 may include a temperature or heater controller 28 to actively control the heater element 22 and/or a cooling element. For example, the thermal control subsystem 20 may include one or more temperature sensors 30 operable to detect a temperature at least proximate the sample holders 16 that is indicative of a temperature of a biochemical reaction within the sample holders 16. For example, the temperature sensor 30 may detect a temperature of the receiver 12 at one or more locations. The temperature or heater controller 28 may compare the temperature detected by the temperature sensor 30 to the desired or set temperature TREF, and produce appropriate control signals (indicated by arrow 32) to adjust operation of the heater element 22. The temperature or heater controller 28 may take a variety of forms including, but not limited to microcontrollers, microprocessors, digital signal processors (DSPs), application specific integrated circuits (ASICs), field programmable gate arrays (FPGAs), comparators, discrete circuit components, or the like. For example, the heater controller 28 may take the form of an ON-OFF controller, for instance an ON-OFF controller commercially available from Minco as part no. Heaterstat, CT198-1007R25L1. In some embodiments, heat 24 is provided through the receiver 12 via one or more channels 34 formed in the receiver 12. This may advantageously spread the heat more evenly throughout the receiver 12.

The isothermal reaction system 10 may include an excitation subsystem 40 operable to excite each of a number of samples 17 contained in respective ones of a plurality of the sample holders 16 with electromagnetic energy while the sample holders 16 are received and supported in the receptacles 14 of the receiver 12. The isothermal reaction system 10 may also include a detection subsystem 42 operable to detect emission of electromagnetic energy from the samples 17 contained in a respective ones of the sample holders 16 while the sample holders 16 are received and supported in the receptacles 14 of the receiver 12.

The excitation subsystem 40 includes a first plurality of excitation sources 44a (collectively 44, only one called out for sake of clarity of illustration). Each of the first plurality of excitation sources 44 is positioned to direct the electromagnetic energy toward at least a portion of a respective one of the sample holders 16 received in a respective one of the receptacles 14 of the receiver 12.

The excitation subsystem 40 may optionally include a second plurality of excitation sources 46a (collectively 46, only one illustrated, removed for sake of clarity of illustration). Each of the second plurality of excitation sources 46 is positioned to direct the electromagnetic energy toward at least a portion of a respective one of the sample holders 16 received in a respective one of the receptacles 14 of the receiver 12. The electromagnetic energy directed by the second plurality of excitation sources 46 may be of a different wavelength or different bands of wavelength than the electromagnetic energy directed by the first plurality of excitation sources 44. In some embodiments, at least one filter 48 (only one illustrated for sake of clarity of drawing) is positioned between at least one excitation source 44, 46 and the at least one of the sample holders 16 when the sample holder 16 is received by a respective receptacle 14 of the receiver 12. For example, the filter 48 may take the form of an amber cast acrylic sheet (e.g., PLEXIGLASS), which forms a very sharp long pass optical filter at approximate 550 nm.

The excitation sources 44, 46 may, for example, take the form of light emitting diodes (LEDs). The LEDs may be operable to emit electromagnetic energy in at least an optical portion of the electromagnetic spectrum between an ultraviolet portion of the electromagnetic spectrum and an infrared portion of the electromagnetic spectrum, inclusive. For example, the first plurality of excitation sources 44 may include a number of LEDs which are operable to emit electromagnetic energy in a first band, and the second plurality of excitation sources 46 may include a number of LEDs which are operable to emit electromagnetic energy in a second band, different than the first band. The bands may be distinct, and these distinct bands may, or may not overlap. Increasingly powerful LEDs in multiple colors with small formats are becoming commercially common. For example, a suitable LED may be commercially available form Sunbrite as SSP-01TWB7UWB12 12V 470 nm Blue LED. Alternatively, all excitations sources 44, 46 may emit at the same wavelengths, and filters used to produce different excitation from the respective excitation sources 44, 46.

In particular, the excitation sources 44, 46 may be positioned at least partially in respective ones of a number of passages 50 (only one called out in FIG. 1, for sake of clarity of illustration) formed in the receiver 12. A portion of each of the excitation sources 44, 46 is proximate (e.g., less than 2 mm, or less than about 1 mm) respective ones of the receptacles 14. This locates the excitation sources 44, 46 close to the sample holders 16, for example within 2 mm or 1 mm, improving analysis and, for at least some methods of amplification making analysis possible where it might not otherwise be possible with conventional excitation sources. In at least one embodiment, each of the excitation sources 44, 46 are positioned with respect to the receiver 12 to direct the electromagnetic energy toward only a base portion 52 of a sidewall of the respective sample holder 16 when the sample holder 16 is positioned in the respective one of the receptacles 14. This may be advantageous since the sample 17 is likely to collect at the bottom of the sample holder 16, under the influence of gravity.

The excitation subsystem 40 may also include an excitation controller 54, operable to control the operation of the excitation sources 44, 46 via appropriate signals (indicated by arrow 56). For example, the excitation controller 54 may control when the excitation sources 44, 46 emit electromagnetic energy. Additionally, or alternatively, the excitation controller 54 may control the duration during which the excitation sources 44, 46 emit electromagnetic energy. Additionally, or alternatively, the excitation controller 54 may control the level or magnitude of electromagnetic energy emitted by the excitation sources 44, 46. Additionally, or alternatively, the excitation controller 54 may control the wavelength or band of wavelengths emitted by the excitation sources 44, 46. The signals 56 may take any of a variety of forms including, but not limited to currents, voltages, impedances, light, radio frequency, and/or microwave signals.

The detection subsystem 42 may include one or more detectors 60a (collectively 60, only one called out for sake of clarity of illustration). Each of the detectors 60 is positioned to detect electromagnetic energy emitted by the sample in a sample holder 16 while the sample holder 16 is received in a respective one of the receptacles 14 of the receiver 12. In some embodiments, at least one filter 62 is positioned between the detectors 60 and the respective sample holder 16 when the sample holder 16 is received by the respective receptacle 14 of the receiver 12. The filter 62 may, for example, substantially block wavelengths emitted by the excitation sources 44, 46, while substantially passing wavelengths emitted by the samples 17 (e.g., fluorescence) in response to the excitation. The filter 62, may for example, take the form of a 532 nm optical band pass filter.

The detectors 60 of the detection subsystem 42 may, for example, take the form of photodiodes, photodetectors, or other electromagnetic sensitive devices. The detectors 60 may, for example, be responsive to electromagnetic energy in at least of a portion of the electromagnetic spectrum between an ultraviolet portion of the electromagnetic spectrum and an infrared portion of the electromagnetic spectrum, inclusive. The detectors 60 may, for example, include a number of photodiodes that are responsive to electromagnetic energy in a portion of the electromagnetic spectrum that is different from the portion of the electromagnetic spectrum in which the excitation sources 44, 46, for example LEDs. A variety of photodiodes may be suitable. For example, a single chip design photodiode with a built in amplifier may be commercially available from Texas Instruments as OPT101. A photodiode with three color detection (RGB) and individual outputs for each color may be commercially available from Hamamatsu as S9702. A line-of-sight or field-of-view of the photodiodes 60 may be arranged perpendicular to a principal direction or axis of emission of the excitation sources 44, 46. Such may prevent the emission by the excitation sources 44, 46 from interfering with or creating excessive noise for the detectors photodiodes 60, reducing or eliminating the need for filtering.

In particular, the detectors 60 may be positioned at least partially in respective ones of a number of openings 64 (only one called out in FIG. 1, for sake of clarity of illustration) formed in a bottom or lower face 63 of the receiver 12. A portion of each of the detectors 60 is proximate (e.g., less than 2 mm, or less than about 1 mm) respective ones of the receptacles 14. This locates the detectors 60 close to the sample holders 16, for example within 2 mm or 1 mm, improving detection and, for at least some methods of amplification, making analysis possible where it might not otherwise be possible with conventional excitation sources and detectors with or without lenses, reflectors or other optical elements. In at least one embodiment, each of the detectors 60 are positioned with respect to the receiver 12 to be proximate the base portion 52 of the respective sample holder 16 when the sample holder 16 is positioned in the respective one of the receptacles 14. This may be advantageous since the sample 17 is likely to collect at the bottom of the sample holder 16, under the influence of gravity. Where the sample holder 16 is not elongated, for example a flat plate or tape, the detectors 60 may alternatively be positioned above the receptacles 14 of the receiver 12.

The detector subsystem 42 may include a detection controller 66, operable to receive and process data detected by the detectors 60. The detection controller 66 may receive signals encoding data or other information (indicated by arrow 67) from the detectors 60. For example, the detection controller 66 may transform analog signals to digital signals. Also for example, the detection controller 66 may otherwise preprocess signals, for instance performing electronic filtering. The signals 67 may take any of a variety of forms including, but not limited to currents, voltages, impedances, light, radio frequency, and/or microwave signals. The detection controller 66 may take a variety of forms, for example hardware, software stored in a storage device, firmware or a combination of such. The detection controller 66 may, for example, be implemented by a general purpose computer executing instructions that cause the general purpose computer to function as a special purpose machine. The detection controller 66 may be implemented as a microcontroller, microprocessor, DSP, ASIC and/or FPGA, or as discrete electrical and/or electronic components.

The detector subsystem 42 may include an analysis subsystem 68. The analysis subsystem 68 may receive raw or preprocessed data or information (indicated by arrow 69) from the detection controller 69. The analysis subsystem 68 may analyze the data 69 according to a variety of known protocols and protocols to be developed. For example, the analysis subsystem 68 may analyze the data 69 for matches between nucleic acids. The analysis subsystem 68 may take a variety of forms, for example hardware, software stored in a computer-readable storage device 65, firmware or a combination of such. The analysis subsystem 68 may, for example, be implemented by a general purpose computer executing instructions that cause the general purpose computer to function as a special purpose machine. The analysis subsystem 68 may be implemented as a microcontroller, microprocessor, DSP, ASIC and/or FPGA, or as discrete electrical and/or electronic components. In some embodiments, the analysis subsystem 68 or its functions may be part of, or implemented by the detection controller 66. In other embodiments, the detection controller 66 or its functions may be part of, or implemented by the analysis subsystem 68. Preprocessing may, for example include real-time signal averaging, followed by non-causal zero phase digital post processing digital filtering. In some embodiments, a differential instrumentation amplifier may be used to interface with a universal serial bus (USB) analog digital converter.

FIGS. 2A-2E show a receiver 12, according to one illustrated embodiment. The receiver 12 may take the form of an elongated metal bar. The receiver 12 may, for example, be formed from aluminum.

In the embodiment illustrated in FIGS. 1 and 2A-2E, the receiver 12 has the plurality of receptacles 14 formed in an upper face 70 of the metal bar. Each of the receptacles 14 has a diameter that is sized to closely receive a diameter of a respective one of the sample holders 16. The receiver 12 may include a pair of angled faces 72a, 72b, each forming an obtuse angle 74a, 74b between with the upper face 70. Each of the angled faces 72a, 72b may have a respective set of passages 50a, 50b (only four of each called out in FIGS. 2B-2D). Each of the passages 50a, 50b extends from an exterior of the receiver 12 to an interior of the receiver 12, providing communication with a respective one of the receptacles 14. Each of the passages 50a, 50b may receive at least a portion of a respective one of the excitation sources 44a, 44b. As noted above, the receiver 12 has a large thermal mass. For example, the receiver 12 may have a thermal mass ten times greater than the thermal mass of the samples 17.

Figure 3:
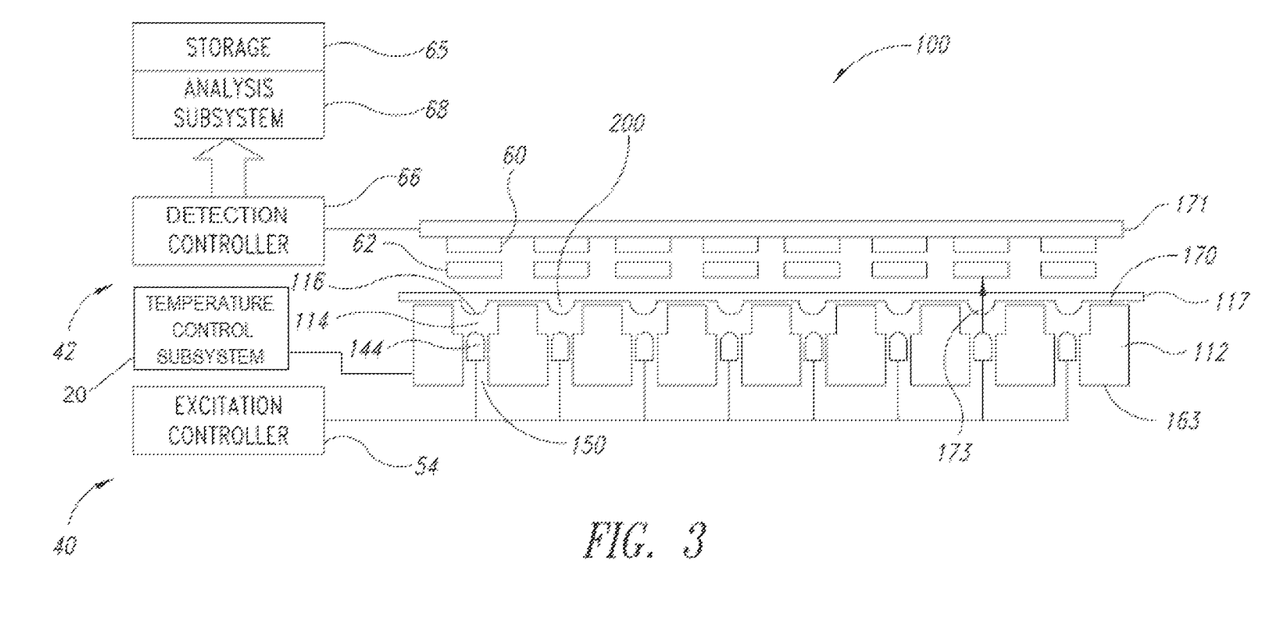
FIG. 3 is a diagrammatic view of an isothermal reaction and analysis system including a receiver to receive sample holders, a thermal control subsystem, an excitation subsystem, a detection subsystem and an analysis subsystem, according to another illustrated embodiment, particularly suited for use with non-elongated sample holders, for example plates or other substrates.

FIG. 3 shows an isothermal reaction and analysis system 100, according to another illustrated embodiment, particularly suited for use with non-elongated sample holders, for example plates or other substrates. Structures which are identical or similar to previously described embodiments are called out with the same reference numbers are previously used.

In particular, a receiver 112 has the plurality of receptacles 114 (only one called out in FIG. 3, for sake of clarity of illustration) formed in an upper face 170 of the metal bar. Each of the receptacles 114 has a diameter that is sized to closely receive a diameter of a respective one of the sample holders. The sample holders may, for example, take the form of wells 116 (only one called out in FIG. 3 for sake of clarity of illustration) formed on a plate, microfluidic cartridge or other substrate 117. Plates or substrates 117 may, for example, be compatible with ANSI/SBS standards 1-2004, 2-2004, 3-2004 and 4-2004. For example, the receptacles 14, 114 may are spaced from one another by a distance selected from 2.25 mm, 4.5 mm and 9 mm.

The receiver 12 may further have a number of passages 150 (only one called out in FIG. 3 for sake of clarity of illustration) formed in a lower face 163 that is opposed to the upper face 170. Each of the passages 150 extends from an exterior of the metal bar to an interior in communication with a respective one of the receptacles 114. Excitation sources, for example LEDs 144 (only one called out in FIG. 3 for sake of clarity of illustration) are positioned at least partially in respective ones of the passages 150 with a portion of each of the LEDs 144 proximate respective ones of the receptacles 114. This locates the LEDs 144 proximate the wells or sample holders 116 when the wells or sample holders 116 are received in the receptacles 114. Such may facilitate analysis, or make analysis possible for some amplification processes where such would not otherwise have been possible using existing excitation sources.

Detectors, for example, photodiodes 160 may be positioned relatively above the receiver 112, aligned with respective receptacles 114. The photodiodes 160 may, for example, be carried by a common substrate, for example a circuit board 171. A line-of-sight or field-of-view of the photodiodes 160 may be arranged collinearly or coaxially or parallel to a principal direction or axis of emission 173 (only one shown for clarity of illustration) of the LEDs 144. Filters 62 may be positioned between the photodiodes 160 and the wells 116 when the wells 116 are received in the receptacles 114. Such may prevent the emission by the LEDs 144 from interfering with or creating excessive noise for the photodiodes 160.

Some embodiments, the system 10, 100 may take the form of a binary format device. In such embodiments, some of the receptacles 14, 114 may receive sample holders 16, 116 holding a reference sample while other receptacles 14, 114 may receive sample holders 16, 116 holding a target sample undergoing reaction and/or analysis. In such an embodiment the system 10, 100 may provide a binary response (e.g., YES/NO, POSITIVE/NEGATIVE). The reference sample may, for example, have a complete amplification mixture without a trigger. A reference signal from the reference sample may be automatically subtracted from the signal representing the unknown sample, for example via an instrument amplifier integrated circuit. The instrument amplifier integrated circuit may turn ON LEDs or other indicators if a voltage difference (i.e., amplification) is detected. 8-pin photodiodes may be coupled via respective 10-pin vertical DIP sockets, allowing the heater or a cooling element to be mounted directly to a main circuit board in the binary format device.

In some embodiments, the excitation sources 44, 46, 144 may be modulated in order to enhance the signal-to-noise ratio at the detectors 16, 116, reduce the effect of background noise, and/or enable multiplexing. For instance, excitation controller 54 may pulsed (ON/OFF) or modulated LEDs 144 at a well defined frequency, and the detected signal obtained by the photodiode 160 or other detector may be Fourier transformed, for example by detection controller 66 or analysis subsystem 68, to identify the component of the response signal at the same frequency as that of the excitation source 44, 46, 144. Such can be used, for example, to eliminate noise from ambient illumination. Similarly, selecting well-defined modulation or pulsing frequencies for the excitation sources 44, 46, 144, and extracting the component of the response at the same frequency enables the signal-to-noise ratio to be improved, even where noise is characterized as having a broad spectrum of frequencies.

In some embodiments, multiplexing may be achieved with respect to the excitation sources 44, 46 and/or detectors 60 using different pulsing or modulation frequencies. Such may allow various frequency components of the detector signal to characterize the response of the sample to different excitation source/filter combinations. This may allow two or more labels (e.g., fluorescent tags or markers) to be detected using a single detector 60, reducing the cost of the device. Each defined frequency component corresponds to the excitation of the appropriate fluorophore by its specific excitation source/filter combination. For example, the excitation controller 54 may operate a first excitation source 44 associated with a receptacle 14 at a first frequency to emit at a first wavelength, and operate a second excitation source 46 associated with the same receptacle 14 at a second frequency to emit at a second wavelength, different from the first wavelength. The sample 71 in the receptacle 14 may have two or more biochemical reactions taking place, a first reaction which produces fluorescence in response to the first wavelength and the second reaction which produces fluorescence in response to the second wavelength. A single detector 60 produces a response signal in response to the fluorescence that results from both the first and second wavelengths of excitation. The detection controller 66 or analysis subsystem 68 may demodulate the response signal based on the first and the second frequencies, to determine information about the first and the second biochemical reactions (e.g., whether reactions occurred, to what extent reactions occurred, products of reactions, etc.). In some embodiments, the excitation controller 54 may operate all of the first plurality of excitations sources 44 at the first frequency and all of the second plurality of excitation sources 46 at the second frequency. In other embodiments, the excitation controller 54 may operate each of excitations sources 44, 46 at a respective frequency. In some embodiments, the excitation controller 54 may vary a current supplied to the excitation sources to vary the emission wavelength of the excitation source. Such may advantageously reduce the total number of excitations sources without reducing the amount of information about the biochemical reactions that may be derived.

In some embodiments, the system 10, 100 may be used to measure the growth of cells that express various fluorescent proteins.

In one embodiment, the system 10, 100 may be constructed by assembly of electronic components and computer numeric controlled (CNC) machining. A 96 well aluminum plate (Biosmith, 81001), designed to accommodate 200 μl tubes, may be cut down in size to provide a row of 8 wells. Two DELRIN plastic parts may be machined (e.g., CNC machined) to provide separate holders for the LED and the combination of the photodetector and optical filter. Each DELRIN part has clearance holes for 4-40 screws, which mate to the aluminum 8 well vessel. Two holes may be tapped in the aluminum 8 well vessel to accommodate 4-40 screws, which align with the DELRIN clearance holes. A 10 MΩ feedback resistor is connected to the output and input pins of the OPT101 photodetector from Texas Instruments. The photodetector may be powered with two 9 Volt batteries for positive and negative supply voltages. Voltage regulators, LM7808 and LM7908 regulate the voltage to the photodetector at positive and negative 8 Volts, respectively. The output of the OPT101 photodetector may be connected to the differential inputs of an INA 118P instrumentation amplifier from Texas Instruments. The gain of the amplifier may be set to 51 using a 1Ω resistor. The output from the OPT101 is connected to the single ended inputs of channel 0 of a USB analog to digital converter (PMD1208LS, Measurement and Computing). A separate 9 Volt battery may supply voltage to an LM7808 voltage regulator, which supplies current to an LED in series with a 470Ω resistor. Holes in the aluminum 8 well vessel may be machined to allow the fluorescence excitation light to penetrate a transparent 200 microliter tube and to allow the emission light to be detected by a photodetector. A thin-film Kapton heater with an aluminum foil backing, purchased from Minco, may be adhered to the side wall of the aluminum 8 well vessel. The heater may be electrically connected to a resistance-matched, Minco on-off controller (Heaterstat, CT198-1007R25L1), which is connected to an AC to DC transformer. The controller may be adjusted to provide a temperature set point required by the reaction. The generic 200 μl tube (Biorad) may be filled with the EXPAR amplification reaction and Sybr Green II. An oligonucleotide sequence to initiate the EXPAR reaction may be added to the sample holder (reaction tube), at 0 degrees C., external to the device. The sample holder (reaction tube) may be placed in the appropriate receptacle of the aluminum 8 well/receptacle vessel. A LABVIEW program may be initiated to average the incoming, sub-volt signal for one second. The result may be plotted and stored to a text file. The resulting text file may be processed by Matlab with a non causal zero phase distortion digital filter routine using a twenty second signal processing window.

In some embodiments, the sample holders 16, 116 may, for example, take the form of Society for Biomolecular Screening (SBS) standard format tubes. Such tubes are typically low cost, and disposable. In some embodiments, the sample holders 16, 116 may take the form of wells formed in plates or other substrates, for example plates or substrates that are compatible with ANSI/SBS standards 1-2004, 2-2004, 3-2004 and 4-2004. In some embodiments, the sample holders 16, 116 may take other forms, with specific geometries and material properties to facilitate reaction, assaying or other functions.

At least a portion of each of the sample holders 16, 116 comprises a material that passes at least a portion of electromagnetic energy emitted by the excitation sources 44, 46, 144 of the excitation subsystem 40. At least a portion of each of the sample holders 16, 116 comprises a material that passes at least a portion of the electromagnetic energy emitted by samples held in the sample holders 16, 116 in response excitation by electromagnetic energy from the excitation sources 44, 46, 144. In this respect, it is noted that the electromagnetic energy emitted by the samples (e.g., florescence) may be different or have a different set or band of wavelengths than the electromagnetic energy emitted by the excitation sources 44, 46, 144 of the excitation subsystem 40. In particular, at least a bottom portion of the sample holder 16, 116 provides an optical path between an exterior of the sample holder 16, 116 and an interior 200 of the sample holder 16, 116. Typically, all or substantially all of the sample holders 16, 116 will be formed of or including a coating of a same material, without a transition of materials along the length or around a perimeter of the sample holders 16, 116. The sample holder may be formed from the filtering material or with the filtering material included, or the filtering material may take the form of one or more coatings or layers applied on an exterior or interior, to become an integral part of the sample holder 16, 116.

In some embodiments, at least a portion of each of the sample holders 16, 116 comprises a material that additionally filters out a portion of electromagnetic energy emitted by the excitation sources 44, 46, 144 of the excitation subsystem 40. Such may advantageously eliminate the use of separate filters 48, 62. For example, such material may substantially block wavelengths that would interfere with the detectors 60, while passing wavelengths that excite the samples. Such may additionally, or alternatively protect the contents of the sample holders 16, 116 from ambient electromagnetic energy.

In some embodiments, at least a portion of the sample holders 16, 116 comprises a material that additionally, or alternatively, filters out a portion of the electromagnetic energy emitted by the samples held in the sample holders 16, 116 in response excitation by electromagnetic energy from the excitation sources 44, 46, 144 of the excitation subsystem 40. In this respect, it is noted that the material may filter out a first wavelength, set or band of wavelengths emitted by the excitation subsystem and may filter out a second wavelength, set or band of wavelengths emitted by samples, where the first and the second wavelengths, set or band of wavelengths are different from one another, which first and second wavelengths, sets or bands of wavelengths may, or may not, be overlapping.

The sample holders 16 may advantageously be sealed during use, preventing contamination. In particular, the sample holder 16 may have an upper portion that is selectively sealable, for example via a cap 202, or adhesive, epoxy or via the sealing of edges forming a perimeter of an opening via heat and/or application of force.

The disclosed embodiments provide a low cost, high speed and effective solution to performing biochemical reactions such as isothermal amplification and/or analysis of the results of such reactions. The disclosed embodiments further provide a reaction and/or analysis device that is light weight, has a small form factor, for example being handheld, and hence is portable. The disclosed embodiments are capable of operating with existing sample holders, avoiding the need to stock multiple types of sample holders or the need to replace existing stocks of sample holders. The disclosed embodiments advantageously permit excitation and detection to occur through the sidewalls of a sample holder, eliminating the need for flat bottom wells or flat lids. Further, the disclosed embodiments allow real time collection and/or analysis of data during biochemical reactions. Such may permit quantification, rather than simply detection of a presence or absence of a reaction product. The disclosed designs allow the elimination of light collecting optics due to the small footprint and positioning of the excitation sources and/or detectors. The disclosed designs advantageously allow simultaneous detection of fluorescence in multiple wells, increasing throughput of the system. The disclosed designs also permit the use of sample holders with relatively small surface-to-volume ratios, compared with PCR thermal cycling devices. The disclosed designs also allow easy integration since excitation and detection may be performed through the base portion of the sidewall of the sample holders.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to isothermal reactors and/or analysis devices, not necessarily the exemplary nucleic acid amplification and analysis device generally described above.

For instance, the foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

In addition, those skilled in the art will appreciate that the mechanisms of taught herein are capable of being distributed as a program product in a variety of forms, and that an illustrative embodiment applies equally regardless of the particular type of signal bearing media used to actually carry out the distribution. Examples of signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A system to support biochemical reactions, comprising:
   a receiver having a plurality of receptacles formed therein, each of the receptacles sized to at least partially receive and support a respective one of a plurality of sample holders;
   an excitation subsystem including at least a first plurality of excitation sources each with a respective axis of emission and positioned at least partially in the receiver to direct electromagnetic energy toward at least a portion of a respective one of the sample holders received in a respective one of the receptacles of the receiver, the excitation subsystem operable to emit electromagnetic energy with a first wavelength sufficient to excite fluorescence in each of a number of samples contained in respective ones of a plurality of the sample holders while the sample holders are received and supported by the receiver;
   a detection subsystem that includes a plurality of detectors, each of the detectors having a respective line of sight and positioned to detect fluorescence emission of electromagnetic energy at wavelength that is different from the first wavlength, emitted by a respective sample contained in a respective one of the sample holders that are received and supported by the receiver, each of the detectors positioned such that the respective line of sight of the detector and the respective axis of emission of the respective excitation source are arranged at an angle to reduce the detection of emission directly from the excitation sources; and
   a thermal control subsystem operable to at least approximately maintain an at least approximately uniform temperature of the receiver at least approximately constant for a period of time sufficient to perform an isothermal reaction on the samples.

2. The system of claim 1 wherein at least one of the plurality of detectors is positioned such that the line of sight of the detector and the axis of emission of the respective excitation source are not coaxial.

3. The system of claim 1 wherein the excitation subsystem includes a second plurality of excitation sources, each of the excitation sources of the second plurality of excitation sources positioned at least partially in the receiver to direct the electromagnetic energy toward at least a portion of a respective one of the sample holders received in a respective one of the receptacles of the receiver, the electromagnetic energy directed by the excitation sources of the second plurality of excitation sources being of a different wavelength than the electromagnetic energy directed by the excitation sources of the first plurality of excitation sources.

4. The system of claim 3 wherein each of the excitation sources is positioned completely within a respective passage in the receiver to direct the electromagnetic energy toward only a base portion of the respective sample holder when the sample holder is positioned in the respective one of the receptacles, the base portion at least proximate a bottom of the sample holder when supported by the receiver.

5. The system of claim 1, further comprising:
at least one filter positioned between at least one excitation source and the at least one of the sample holders when the at least one of the sample holders is received by the respective receptacle of the receiver.

6. The system of claim 1, further comprising:
at least one filter positioned between at least one of the detectors and the at least one of the sample holders when the at least one of the sample holders is received by the respective receptacle of the receiver, the at least one filter operative to filter at least a portion of the electromagnetic energy emitted by at least one of the excitation sources.

7. The system of claim 1 wherein the thermal control subsystem includes at least one temperature sensor operable to detect a temperature at least proximate the sample holders that is indicative of a temperature of a biochemical reaction within the sample holders and at least one heater element operable to provide heat to the receiver in response to a difference between the detected temperature and at least one set temperature.

8. The system of claim 7 wherein the at least one heater element is conductively thermally coupled to the receiver to provide heat to the sample holders via the receiver.

9. The system of claim 8 wherein the receiver has a large thermal mass with respect to the samples.

10. The system of claim 1 wherein the excitation subsystem includes a number of light emitting diodes at least some of which are operable to emit electromagnetic energy in at least two distinct bands.

11. The system of claim 1 wherein the detectors of the detection subsystem include a number of photodiodes that are responsive to electromagnetic energy in a portion of the electromagnetic spectrum between an ultraviolet portion of the electromagnetic spectrum and an infrared portion of the electromagnetic spectrum, inclusive.

12. The system of claim 1 wherein the excitation subsystem includes a number of light emitting diodes at least some of which are operable to emit electromagnetic energy in a portion of the electromagnetic spectrum between an ultraviolet portion of the electromagnetic spectrum and an infrared portion of the electromagnetic spectrum, inclusive.

13. The system of claim 1, further comprising:
the plurality of sample holders, wherein each of the sample holders comprises a material that filters out a portion of electromagnetic energy emitted by the excitation subsystem and passes a portion of electromagnetic energy emitted by the excitation subsystem.

14. The system of claim 1 wherein the receptacles are spaced from one another by a distance selected from 2.25 mm, 4.5 mm and 9 mm.

15. The system of claim 1, further comprising:
at least one controller configured to provide control signals to at least one of modulate or pulsate the excitation sources and to select a component of a response signal from the detection elements based on the modulation or pulsation of the excitation sources.

16. The system of claim 1 wherein the at least one controller is configured to perform Fourier transformation on the response signal to improve a signal-to-noise ratio of the system.

17. The system of claim 1, further comprising:
at least one controller configured to provide respective control signals to at least one of modulate or pulsate the excitation sources at respective frequencies and to select a component of a response signal from the detection elements based on the modulation or pulsation of the excitation sources.

18. The system of claim 1 wherein there are at least two excitation sources and one detector per receptacle, where each of at least two of the excitation sources per receptacle emit at different wavelengths, and further comprising:
at least one controller configured to operate a first one of the two excitations sources of a first receptacle at a first frequency and a second one of the excitation sources of the first receptacle at a second frequency, different from the first frequency, and to demodulate a response signal from the detector based on the first and the second frequencies.

19. The system of claim 18 wherein the at least one controller is configured to determine at least one piece of information about a first biochemical reaction occurring in the first receptacle and at least one piece of information about a second biochemical reaction occurring in the first receptacle based on the demodulated response signal.

20. The system of claim 1, further comprising:
at least one controller configured to vary a current supplied to the excitation sources to cause each of the excitation sources to emit a first wavelength at a first time and a second wavelength different from the first wavelength at a second time.

21. The system of claim 1 wherein the biochemical reaction is an isothermal amplification reaction and the sample comprises nucleic acids.

* * * * *